United States Patent [19]

Kitamori et al.

[11] Patent Number: 4,890,925
[45] Date of Patent: Jan. 2, 1990

[54] METHOD AND APPARATUS FOR DETECTING PARTICULAR PARTICULATE SUBSTANCE

[75] Inventors: Takehiko Kitamori, Hitachi; Kazuo Yasuda, Katsuta; Yasushi Nomura; Kazumichi Suzuki, both of Mito; Haruo Fujimori, Hitachi, all of Japan

[73] Assignee: Hitachi, Ltd., Tokyo, Japan

[21] Appl. No.: 83,197

[22] Filed: Aug. 10, 1987

[30] Foreign Application Priority Data

Aug. 11, 1986 [JP] Japan ................... 61-186808

[51] Int. Cl.⁴ ............................................ G01N 21/00
[52] U.S. Cl. ..................... 356/432; 356/36; 356/336; 356/440; 356/442
[58] Field of Search ............... 356/432, 432 T, 440, 356/441, 442, 335, 336, 36

[56] References Cited

U.S. PATENT DOCUMENTS 4,747,685  5/1988  Suzuki ..................... 356/336

FOREIGN PATENT DOCUMENTS 159648  8/1985  Japan .
102541  5/1986  Japan .

OTHER PUBLICATIONS

Tam et al.: "Measurement of Small Absorptions in Liquids", Optics Letters, vol. 4, No. 3 (Mar. 1979), pp. 81–83.
Oda et al, "Simultaneous Determination of Mixtures in Liquid by Laser-Induced Photoacoustic Spectroscopy", Analytical Chemistry, vol. 51, No. 6 (May 1979), pp. 686–688.
Sawada et al, "Laser-Induced Photoacoustic Spectroscopy of Some Rare Earth Ions on Aqueous Solutions", Analytical Chemistry, vol. 51, No. 6 (May 1979), pp. 688–690.

Primary Examiner—Richard A. Rosenberger
Attorney, Agent, or Firm—Antonelli, Terry & Wands

[57] ABSTRACT

By use of an excitation beam having a wavelength which is equal to, or close to, the sizes of particular particulate substances as the object of analysis, the particulate substances such as an immunoreaction product between an antigen and an antibody or between the antigen and a material supporting the antibody thereon are detected selectively. Very small particles having specific sizes such as rheumatuid factors, cancer specific antigens can be detected with high sensitivity.

64 Claims, 5 Drawing Sheets

BEFORE REACTION

FIG. 6(B)

AFTER REACTION

FIG. 7

METHOD AND APPARATUS FOR DETECTING PARTICULAR PARTICULATE SUBSTANCE

BACKGROUND OF THE INVENTION

This invention relates to a method and apparatus for detecting a particulate substance in a liquid and more particularly to a detection method and apparatus of an immunoreaction product which may be suitable for detecting a trace amount of an immunoreaction product.

Conventional methods and apparatuses for detecting very small particles in a liquid in accordance with photoacoustic spectroscopy are not equipped with a control mechanism which controls the wavelength of excitation light in such a manner as to bring it into conformity with the size of the very small particules as the object of measurement, as can be seen, for example, from Japanese Patent Laid-Open No. 102541/1986. They do not either consider any mechanism which detects selectively particulate substaces having a specific size dependence of sensitivity of an photoacoustic spectrometry and determines the quantity of the particulate substances. Therefore, the prior art technique does not consider selective detection and determination of a reaction product such as an immunoreaction product in the system where an antibody, antibody support particles and reaction products coexist during non-reaction.

The prior art technique described above does not take into consideration the particle size dependency of sensitivity of the photoacoustic spectrometry and cannot selectively detect and determine very small particles having specific sizes such a rheumatuid factors, cancer specific antigens, and the like.

SUMMARY OF THE INVENTION

It is therefore an object of the present invention to provide a method and apparatus for detecting and determining very small particles having specific sizes in a liquid and more particularly, for determining selectively and highly sensitive immunoreaction products.

The object described above can be accomplished in the following way. The sensitivity of an photoacoustic spectrometry to particulate substances as the object of analysis is increased by use of excitation beam having a wavelength which is in agreement with, or close to, the sizes of the particulate substances as the object of analysis by utilizing the size dependence of the sensitivity of photoacoustic spectroscopy which is found out by the present inventors, and the particulate substance are then detected and determined selectively. The object described above can be accomplished, too, by controlling the sizes of the resulting particulate substances so that they coincide with the wavelength of excitation beam of the photoacoustic spectroscope.

DETAILED DESCRIPTION OF THE PREFERRED EMBODIMENTS

Hereinafter, the principle of the present invention will be described.

Figure 1:
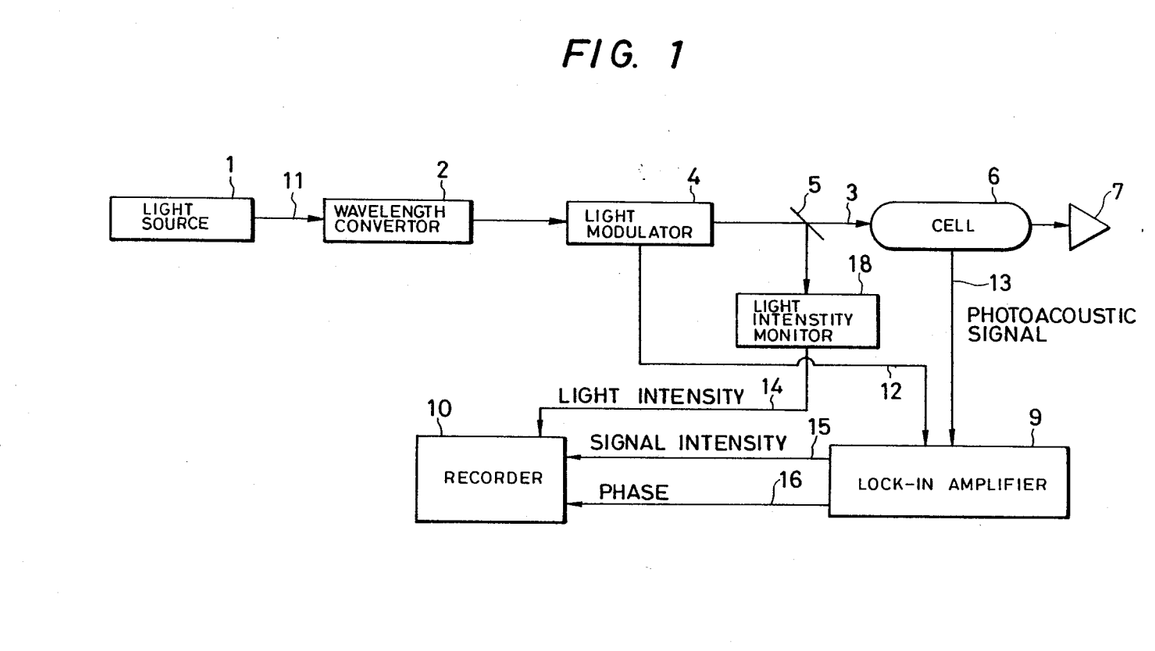
FIG. 1 is a block diagram showing the fundamental construction of a particulate substance determination apparatus in a liquid in accordance with the present invention.

FIG. 1 shows one example of the fundamental construction of a detector for an immunoreaction product in accordance with the present invention. The ray of light 11 from a light source 1 such as laser is converted to excitation light 3 having a wavelength which is equal to, or near, the size of a particulate substance as the object of analysis by a wavelength convertor 2 consisting of a dye laser, a non-linear type optical element, spectrometer, and the like. The ray of light is then incident to a cell 6. The particulate substance contained in a liquid sample inside the cell 6 absorbs the excitation light and generates an photoacoustic signal. The resulting photoacoustic signal is detected by a detector such as a piezoelectric device that is fitted to the cell. The detected photoacoustic signal 13 is amplified by a lock-in amplifier 9 in accordance with a reference signal 12 from an light modulator 4 such as an optical chopper.

The magnitude of the photoacoustic signal measured by such a photoacoustic spectrometry is proportional to the quantity (concentration) of the particulate substance contained in the sample. Therefore, a calibration curve of the particulate substance in accordance with the magnitude of the photoacoustic signal can be obtained.

Figure 2:
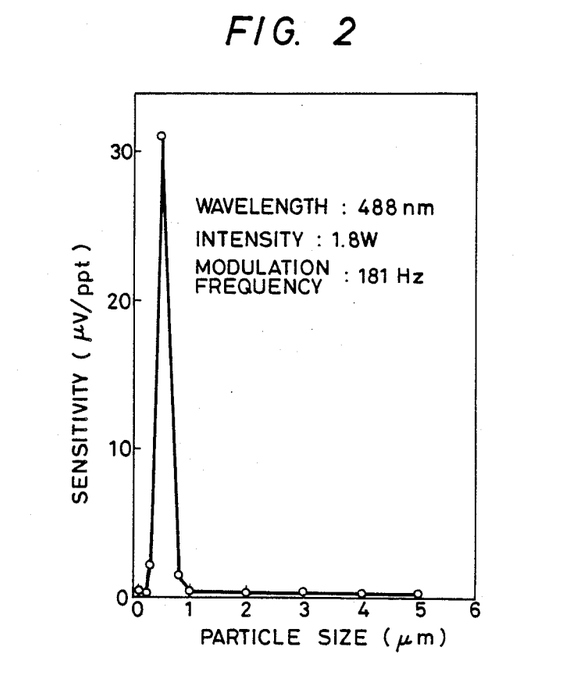
FIG. 2 is a diagram showing particle size dependence of sensitivity of an photoacoustic spectrometry.

Next, FIG. 2 shows particle size dependence of the photoacoustic spectroscope, that is, the slope of the calibration curve. The diagram shows the result of measurement of polystyrene particles. Measurement was performed at the intensity of excitation light of 0.8 W, a wavelength of 488 nm and modulation frequency of 181 Hz. As shown in FIG. 2, it was found for the first time that when the particle size coincides with the wavelength 488 nm (approx. 0.5 $\mu$m) of excitation light, the sensitivity of the photoacoustic spectrometry increases resonantly. This experimental result reveals that when the wavelength of excitation light 3 of the photoacoustic spectrometry shown in FIG. 1 is made to be equal to the particle size of the particulate substance as the object of analysis, particles having a specific size can be detected and determined selectively. Particularly in the case of detection of an immunoreaction product as the particulate substance, the reaction product can be measured selectively and with high sensitivity even when unreacted antibodies or particles supporting the unreacted antibodies coexist, if the wavelength of excitation light is selected in such a manner that it is in agreement with the size of the reaction product but is out of agreement with the size of the antibody or that of the particle supporting the antibody.

Particle size dependence of sensitivity shown in FIG. 2 presumably results from the fact that dielectric loss due to particles increases resonantly at the wavelength which is in agreement with the particle size and near that wavelength in the same way as scattering of resonant light and heat resulting from the dielectric loss increases resonantly, too, so that the magnitude of the photoacoustic signal generated from the heat released to the medium increases resonantly.

Hereinafter, one embodiment of the present invention will be explained with reference to FIGS. 3 to 7.

Figure 3:
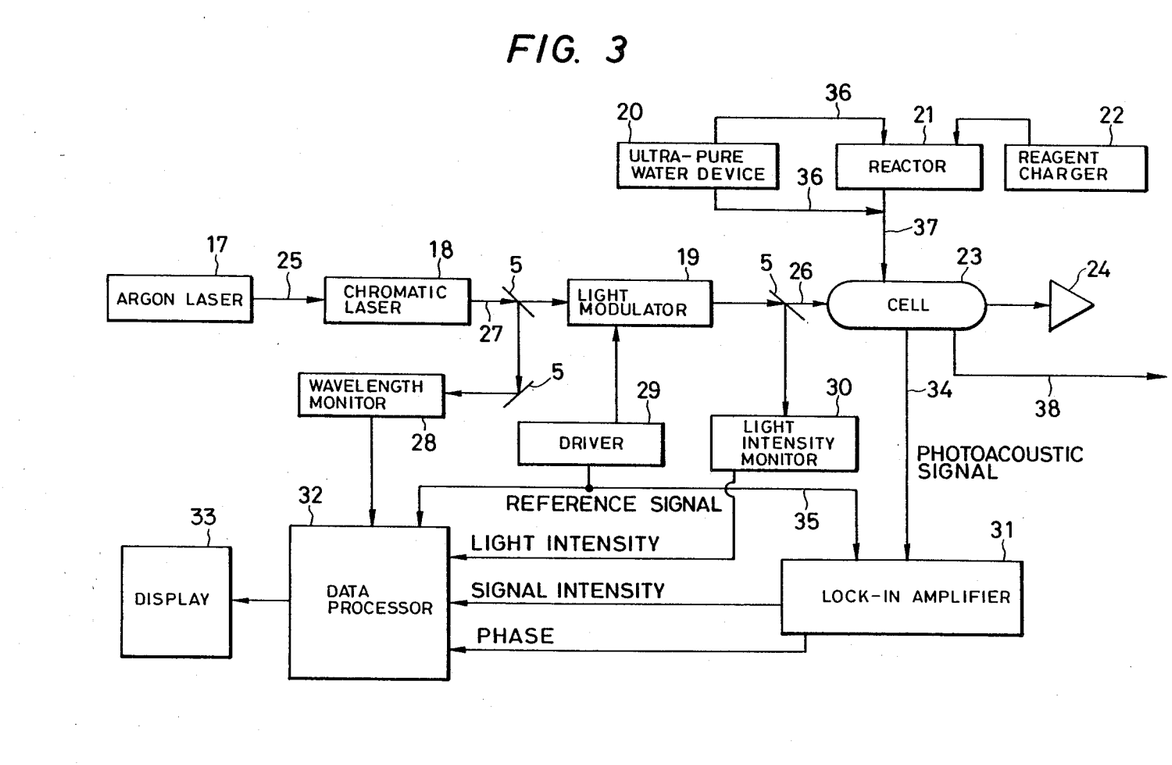
FIG. 3 is a structural view of one embodiment of the present invention.

FIG. 3 shows the construction of a detector for an immunoreaction product in accordance with the present invention. An excitation beam source is an argon laser 17 having a 10 W output and laser beam 25 from the argon laser is emission lines of 488 nm, 514.5 nm and a line of ultraviolet wavelength range. A pigment inside a dye laser 18 is excited (pumped) in accordance with the size of the reaction product as the object of analysis. When the size of the reaction product is from 0.6 to 0.7 μm, for example, the wavelength of the excitation beam 25 from the argon laser 17 is set to 514.5 nm while Rhodamine is used as the pigment of the dye laser 18. Part of the laser beam 27 whose wavelength is converted in accordance with the size of the object of analysis is branched by a half mirror 5, and is incident to a wavelength monitor 28 and its wavelength is confirmed by a wavelength monitor 28. The remaining laser light is subjected to light modulation to a periodical rectangular wave by an intensity modulator 19 consisting of a rotating blade type optical chopper and changes to excitation beam 26. This beam 26 is incident to a cell 23 and lets the sample inside the cell generate an photoacoustic signal. The photoacoustic signal generated in the cell 23 is detected by a piezoelectric element and is amplified by a lock-in amplifier 31 in accordance with a signal 35 from a driver 29 of the light modulator 19. Part of the excitation beam 26 is branched by the half mirror 5 and its intensity is monitored by an optical intensity monitor 30.

The lock-in amplifier 31 inputs information relating to the magnitude and phase of the photoacoustic signal while the wavelength monitor 28, the driver 29 of the light modulator and the optical intensity monitor 30 input information relating to the wavelength of the excitation beam, the modulation frequency and intensity, to a data processor 32. The data processor 32 displays the information of parameters relating to the measurement condition such as the excitation beam wavelength and the modulation frequency on a display 33 or processes the data of the measurement result and displays the calibration curve of the reaction product and the result of determination of an unknown sample on the display 33. The sample such as serum is placed in a reaction tube inside the reactor 21 and the antibody or particles supporting antibody is added by a reagent charger 22. The reaction product formed under the predetermined reaction condition is moved from the reactor 21 to the cell 23 through a sample path 37. After measurement, the sample path 37 is washed by ultrapure water from a ultra-pure water device 20 together with the cell 23 and the next measurement is prepared. The apparatus of the present invention measures automatically a plurality of samples and processes the data by repeating these processes.

Figure 4A:
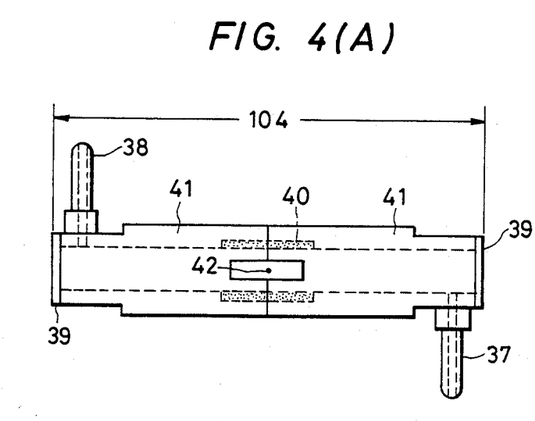
FIG. 4 is a structural view of a cell used in an embodiment of the invention.
Figure 4B:
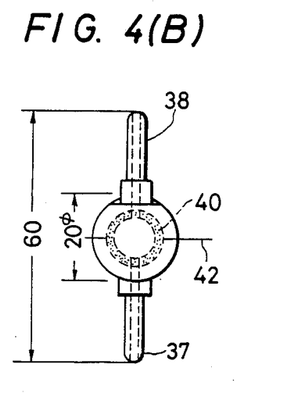

FIGS. 4(A) and 4(B) show a detailed view of the cell 23 of the present apparatus. The inside of the cell is cylindrical. After the sample is packed into the cylinder, the excitation beam 26 is allowed to be incident along the center axis of the cylinder. The photoacoustic signal generated inside the cell is detected by the piezoelectric element 40 and sent as a piezoelectric signal from an electrode terminal 42 to the lock-in amplifier 31. The piezoelectric element is disposed at the center of the cell 23 and its inner diameter is the same as that of the glass cylinder 41 of the cell, and the inside of the cell describes a smooth cylindrical shape. The sample flows into the cell through an inlet tube 37 and after measurement, is discharged to a drain through an outlet tube 38.

Figure 5:
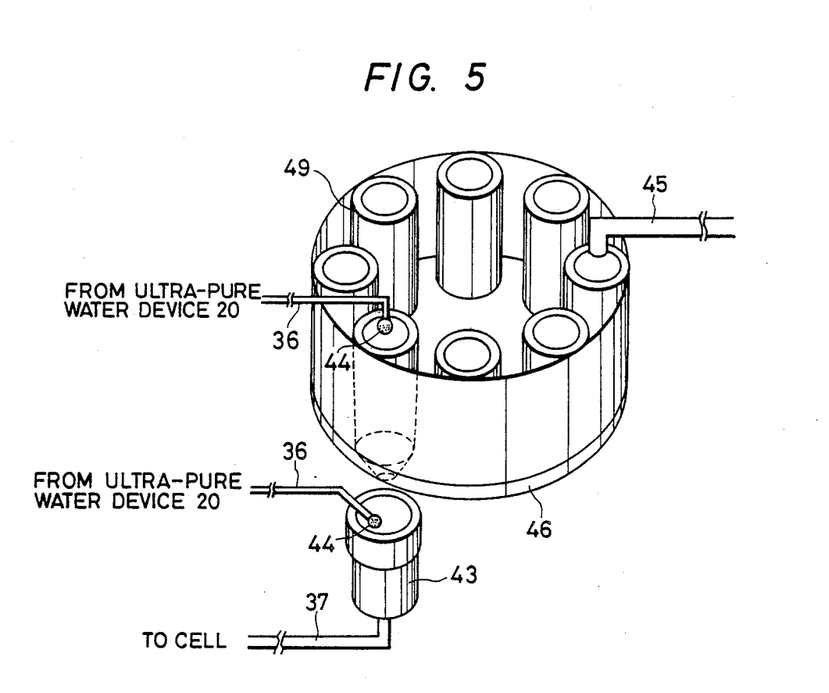
FIG. 5 is a structural view of a reactor and a sample introduction device used for the embodiment.

FIG. 5 shows in detail the reactor 21 of the present apparatus and a sample introduction portion 45. The reactor 21 consists of a reaction tube 49 and a rotary holder 46. A sample such as serum is placed into the reaction tube 49 and the reagent such as the antibody is charged, too, through the reagent charger 22. A stirring device such as a stirrer may be disposed inside the reaction tube 49, whenever necessary. After the reaction, the sample is caused to flow into the sample introduction portion 43 from an extraction port at the lower part of the reaction tube 49 and sent into the cell. After the reaction, the reaction tube 49, the sample introduction portion 43, the sample flow path 37 and the cell 23 are washed by ultrapure water emitted from a spray 44.

Figure 6A:
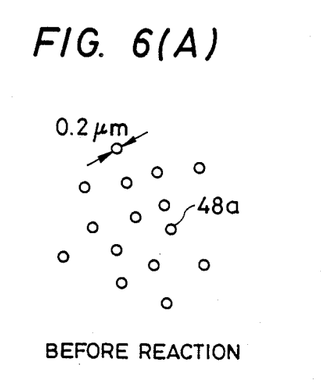
FIG. 6 is a schematic view of polystyrene particles supporting thereon an antibody before and after reaction.
Figure 6B:
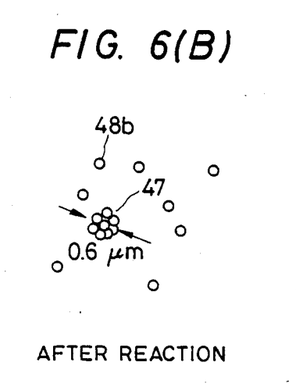

FIGS. 6(A) and 6(B) are schematic views of a material supporting the antibody to be used in the present invention and the reaction product after immunoreaction. The material supporting the antibody is preferably one that has a specific gravity near 1, can be dispersed uniformly into the serum and exhibits a large exothermic quantity due to dielectric loss. From this aspect, polystyrene particles are particulate substance which is suitable for the apparatus of the present invention. The particle diameter of the polystyrene particles 48a supporting the antibody before reaction is set to be 0.2 μm. Since this embodiment is directed to detect a rheumatuid factor, the corresponding antibody is supported on the polystyrene particles 48a. As a result of the immunoreaction under a suitable reaction condition, the polystyrene particles 48a agglutinate through the antigen and turn to the reaction product 47. The size of the reaction product is about 0.5 m and it coexists with the unreacted polystyrene particles 48b.

Since the size of the unreacted particles 48b is 0.2 μm and that of the reaction product is 0.6 μm in this embodiment, the wavelength of the laser beam 25 from the argon laser 17 is set to be 514.4 nm so that the wavelength of the excitation beam becomes 0.6 μm, and hodamine is selected as the pigment of the dye laser 18. The modulation frequency is set to 181 Hz.

Figure 7:
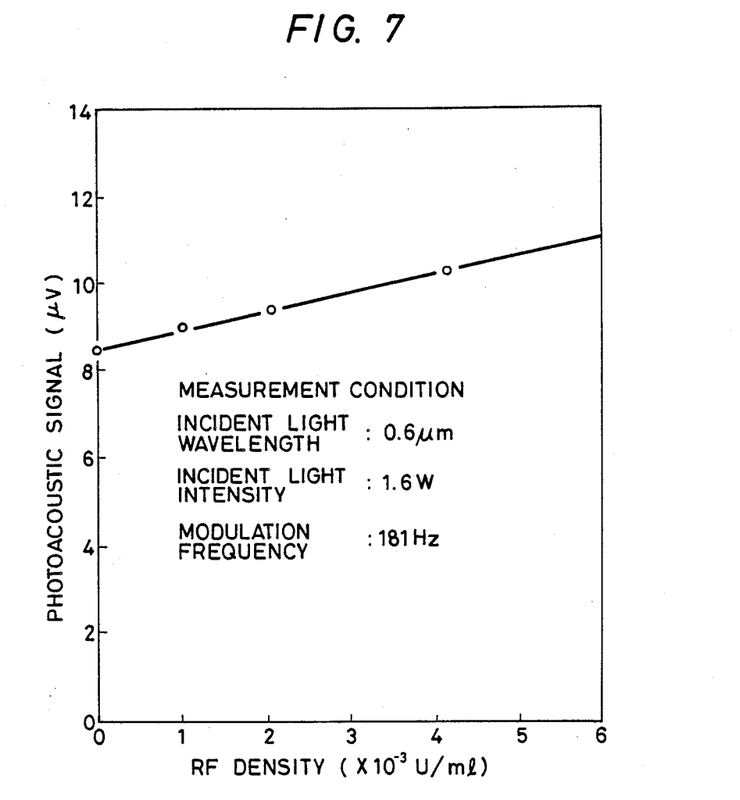
FIG. 7 is a diagram showing a calibration curve of a rheumatuid factor.

FIG. 7 shows an example of the calibration curve of the rheumatuid factor obtained by the present apparatus. It can be understood from the result of measurement that the immunoreaction product can be determined in the concentration range of $10^{-3}$ U/ml (U: international unit). This result represents that the immunoreaction product can be measured in a concentration range which is incomparably lower than the lower determination limit obtained by ordinary turbiditmetry. In the conventional photoacoustic spectroscopes for liquid which cannot select the wavelength, the unreacted product and the reaction product cannot be distinguished and the total amount of the particulate substances in the sample are measured. Therefore, the calibration curve cannot be obtained.

In accordance with the present apparatus, the wavelength can be scanned in the visible range so that the size of the reaction product in the sample can be known from the wavelength providing the peak of signal intensity by monitoring the signal intensity while scanning the wavelength. In this case, the excitation light intensity at each wavelength is monitored by the light intensity monitor and the signal magnitude is standardized. The wavelength that provides the peak is displayed on the display 33 after scanning of the wavelength is complete. Therefore, the wavelength thus displayed can be used for the determination of the reaction product.

The present invention can measure the phase of the photoacoustic signal by the lock-in amplifier 31. The photoacoustic signal generated from the particulate substance in the liquid has a phase corresponding to the size of the particle. This phase depends on the heat radiation time from the particle to the medium and according to the studies made by the present inventors, is a function of the square of the size. Therefore, if the polystyrene particles are 0.2 μm in diameter before the reaction and the reaction proceeds, the reaction product of 0.6 μm in size increases. The present apparatus can monitor the progress of the reaction and the quantity of the reaction product or can detect and determine the reaction product by measuring the change of the phase. In this case, the modulation frequency of the excitation light intensity is set to about 10 KHz in order to increase the variation of the phase.

Next, the case where two wavelengths, that is, the wavelength 0.6 μm which is in agreement with the size of the reaction product and the wavelength 0.2 μm which is in agreement with the size of the unreacted particles, are utilized as the wavelength of the excitation light, will be described. When measurement is made using the wavelength 0.6 μm, the apparatus has sensitivity of about 1/100 of the 0.6 μm particles to the unreacted 0.2 μm particles. Therefore, when the amount of the unreacted particles becomes about 100 times that of the reaction product, the signal component from the unreacted particles, that is, the background, becomes substantially equal to the signal component from the reaction product and determination of the reaction product becomes difficult. Therefore, 0.2 μm particles are determined by the 0.6 μm excitation light exhibiting high sensitivity to the 0.2 μm particles and the data thereby obtained is reduced from the data obtained by using the 0.6 μm excitation light. In this manner, the background of the 0.2 μm particles can be reduced and the reaction product can be determined.

Since the present invention can selectively detect particulate substance having a specific size in the liquid and can determined it with high sensitivity, the invention provides the following effects.

(1) The invention can determined the amount of the immunoreaction product with a by far higher level of sensitivity than conventional tubidimetry.

(2) The present invention can determine a cancer or tumor maker antigen, whose determination has been difficult conventionally, and makes it possible to find diseases such as cancer at an earlier stage.

We claim:

1. A method of detecting a particular particulate substance comprising the steps of:
   adjusting or selecting a wavelength of a ray of light to be substantially equal to the size of the particular particulate substance;
   radiating the ray of light to the particulate substance; and
   measuring the magnitude of a photoacoustic signal generated from the particulate substance.

2. A method according to claim 1, wherein said particulate substance is an immunoreaction product between an antigen and an antibody or between the antigen and a material supporting the antibody thereon.

3. A method according to claim 2, wherein the ray of light to be radiated to the particulate substance is a ray of continuous light within a wavelength range capable of embracing the particulate size distribution of the particulate substance.

4. A method according to claim 2, wherein the support material for tha antibody is a material having a small light absorption coefficient for the wavelength of the ray of light to be radiated.

5. A method according to claim 1, wherein said particulate substance is an immunoreaction product between an antibody and an antigen or between the antibody and a material supporting the antigen thereon.

6. A method according to claim 5, wherein the ray of light to be radiated to the particulate substance is a ray of continuous light within a wavelength range capable of embracing the particulate size distribution of the particulate substance.

7. A method according to claim 5, wherein the support material for said antibody is a material having a small light absorption coefficient for the wavelength of the ray of light to be radiated.

8. A method according to claim 1, wherein the ray of light to be radiated to the particulate substance is a ray of continuous light with a wavelength range capable of embracing the particulate size distribution of the particulate substance.

9. A method of detecting a particular particulate substance comprising the steps of:
   adjusting or selecting a wavelength of a ray of light to be substantially equal to the size of the particular particulate substance;
   radiating the ray of light to the particulate substance;
   measuring the magnitude of a photoacoustic signal generated from the particular substance; and
   determining the concentration of the particulate substance by use of a relationship between the magnitude of photoacoustic signals and the concentration of a particular particulate substance.

10. A method according to claim 9, wherein the particular substance is an immunoreaction product between an antigen and an antibody or between the antigen and a material supporting the antibody thereon.

11. A method according to claim 10, wherein the ray of light to be radiated to the particulate substance is a ray of continuous light within a wavelength range capable of embracing the particle size distribution of the particulate substance.

12. A method according to claim 10, wherein the support material for the antibody is a material having a small light absorption coefficient for the wavelength of the ray of light to be radiated.

13. A method according to claim 9, wherein the particulate substance is an immunoreaction product between an antibody and an antigen or between the antibody and a material supporting the antigen thereon.

14. A method according to claim 13, wherein the ray of light to be radiated to the particulate substance is a ray of continuous light within a wavelength range capable of embracing the particle size distribution of the particulate substance.

15. A method according to claim 13, wherein the support material for the antibody is a material having a small light absorption coefficient for the wavelength of the ray of light to be radiated.

16. A method according to claim 9, wherein the ray of light to be radiated to the particulate substance is a ray of continuous light within a wavelength range capable of embracing the particle size distribution of the particulate substance.

17. A method of detecting a particular particulate substance comprising the steps of:
radiating a ray of light of a wavelength selected to be substantially equal to the size of the particular particulate substance to the particulate substance; and
measuring the magnitude of a photoacoustic signal generated from the particulate substance.

18. A method according to claim 17, wherein the particulate substance is an immunoreaction product between the antigen and an antibody or between the antigen and a material supporting the antibody thereon.

19. A method according to clam 18, wherein the ray of light to be radiated to the particulate substance is a ray of continuous light within a wavelength range capable of embracing the particle size distribution of the particulate substance.

20. A method according to claim 18, wherein the support material for the antibody is a material having a small light absorption coefficient for the wavelength of the ray of light to be radiated.

21. A method according to claim 17, wherein the particulate substance is an immunoreaction product between an antibody and an antigen or between the antibody and a material supporting the antigen thereon.

22. A method according to claim 21, wherein the ray of light to be radiated to the particulate substance is a ray of continuous light within a wavelength range of embracing the particle size distribution of the particulate substance.

23. A method according to claim 21, wherein the support material for the antibody is a material having a small light absorption coefficient for the wavelength of the ray of light to be radiated.

24. A method according to claim 17, wherein the ray of light to be radiated to the particulate substance is a ray of continuous light within a wavelength range capable of embracing the particle size distribution of the particulate substance.

25. A method of detecting a particular particulate substance comprising the steps of:
radiating a ray of a light of wavelength selected to be substantially equal to the diameter of the particular particulate substance to the particulate substance, and
measuring the magnitude of a photoacoustic signal generated from the particulate substance; and
determining the concentration of the particulate substance by use of a relationship between the magnitude of photoacoustic signals and the concentration of a particular particulate substance.

26. A method according to claim 25, wherein the particulate substance is an immunoreaction product between an antigen and an antibody or between the antigen and a material supporting the antibody thereon.

27. A method according to claim 26, wherein the ray of light to be radiated to the particulate substance is a ray of continuous light within a wavelength range capable of embracing the particle size distribution of the particulate substance.

28. A method according to claim 26, wherein the support material for the antibody is a material having a small light absorption coefficient for the wavelength of the ray of light to be radiated.

29. A method according to claim 25, wherein the particulate substance is an immunoreaction product between an antibody and an antigen or between the antibody and a material supporting the antigen thereon.

30. A method according to claim 29, wherein the ray of light to be radiated to the particulate substance is a ray of continuous light within a wavelength range capable of embracing the particle size distribution of the particulate substance.

31. A method according to claim 29, wherein the support material for the antibody ia a material having a small light absorption coefficient for the wavelength of the ray of light to be radiated.

32. A method according to claim 25, wherein the ray of light to be radiated to the particulate substance is a ray of continuous light within a wavelength range capable of embracing the particle size distribution of the particulate substance.

33. A method of detecting a particular particulate substance comprising the steps of:
adjusting or selecting the size of the particular particulate substance to be substantially equal to the wavelength of a ray of light;
radiating the ray of light to the particular substance; and
measuring the magnitude of a photoacoustic signal generated from the particulate substance.

34. A method according to claim 33, wherein the particulate substance is an immunoreaction product between an antigen and an antibody or between the antigen and an material supporting the antibody thereon.

35. A method according to claim 34, wherein the ray of light to be radiated to the particulate substance is a ray of continuous light within a wavelength range capable of embracing the particle size distribution of the particulate substance.

36. A method according to claim 34, wherein the support material for the antibody is a material having a small light absorption coefficient for the wavelength of the ray of light to be radiated.

37. A method according to claim 33, wherein the particulate substance is an immunoreaction product between an antibody and an antigen or between the antibody and a material supporting the antigen thereon.

38. A method according to claim 37, wherein the ray of light to be radiated to the particulate substance is a ray of continuous light within a wavelength range capable of embracing the particle size distribution of the particulate substance.

39. A method according to claim 37, wherein the support material for the antibody is a material having a small light absorption coefficient for the wavelength of the ray of light to be radiated.

40. A method according to claim 33, wherein the ray of light to be radiated to the particulate substance is a ray of continuous light within a wavelength range capable of embracing the particle size distribution of the particulate substance.

41. An apparatus for detecting a particular particulate substance comprising:
a light source;
wavelength converter means for converting a wavelength of a ray of light provided from said light source to a wavelength selected to be substantially equal to the size of said particular particulate substance;
a cell into which said particular substance is charged and which receives the ray of light whose wavelength is converted, and outputs a photoacoustic signal;

a data processor for inputting said photoacoustic signal and discriminating and outputting a photoacoustic signal generated from said particular particulate substance.

42. An apparatus according to claim 41, wherein said particulate substance is an immunoreaction product between an antigen and an antibody or between the antigen and a material supporting the antibody thereon.

43. An apparatus according to claim 42, wherein the ray of light to be radiated to said particulate substance is a ray of continuous light within a wavelength range capable of embracing the particle size distribution of said particulate substance.

44. An apparatus according to claim 42, wherein said support material for said antibody is a material having a small light absorption coefficient for the wavelength of the ray of light to be radiated.

45. An apparatus according to claim 41, wherein said particulate substance is an immunoreaction product between an antibody and an antigen or between the antibody and a material supporting the antigen thereon.

46. An apparatus according to claim 45, wherein the ray of light to be radiated to said particulate substance is a ray of continuous light within a wavelength range capable of embracing the particle size distribution of said particulate substance.

47. An apparatus according to claim 45, wherein said support material for said antibody is a material having a small light absorption coefficient for the wavelength of the ray of light to be radiated.

48. An apparatus according to claim 41, wherein the ray of light to be radiated to said particulate substance is a ray of continuous light within a wavelength range capable of embracing the particulate size distribution of said particulate substance.

49. An apparatus for detecting a particular particulate substance comprising:
- a light source;
- wavelength converter means for converting a wavelength of a ray of light provided from said light source to a wavelength selected to be substantially equal to the size of said particular particulate substance;
- a cell into which said particulate substance as the object of analysis is charged and which receives the ray of light whose wavelength is converted, and outputs a photoacoustic signal;
- a data processor for inputting said photoacoustic signal and determining the concentration of said particulate substance by use of a relationship between the magnitude of photoacoustic signals and the concentration of a particular particulate substance that is previously stored therein; and
- a display for displaying the output information of said date processor.

50. An apparatus according to claim 49, wherein said particulate substance is an immunoreaction product between an antigen and an antibody or between the antigen and a material supporting the antibody thereon.

51. An apparatus according to claim 50, wherein the ray of light to be radiated to said particulate substance is a ray of continuous light within a wavelength range capable of embracing the particle size distribution of said particulate substance.

52. An apparatus according to claim 50, wherein said support material for said antibody is a material having a small light absorption coefficient for the wavelength of the ray of light to be radiated.

53. An apparatus according to claim 49, wherein said particulate substance is an immunoreaction product between an antibody and an antigen or between the antibody and a material supporting the antigen thereon.

54. An apparatus according to claim 53, wherein the ray of light to be radiated to said particulate substance is a ray of continuous light within a wavelength range capable of embracing the particle size distribution of said particulate substance.

55. An apparatus according to claim 53, wherein said support material for said antibody is a material having a small light absorption coefficient for the wavelength of the ray of light to be radiated.

56. An apparatus according to claim 49, wherein the ray of light to be radiated to said particulate substance is a ray of continuous light within a wavelength range capable of embracing the particle size distribution of said particulate substance.

57. An apparatus for detecting a particular particulate substance comprising:
- means for radiating a ray of light of a wavelength selected to be substantially equal to the size of said particular particulate substance to said particulate substance;
- a cell into which said particulate substance as the object of analysis is charged and which receives the ray of light from said radiating means, and outputs a photoacoustic signal;
- a reactor for reacting a sample and a reagent;
- means for moving said sample including an immunoreaction product from said reactor to said cell; and
- a data processor for inputting said photoacoustic signal and discriminating and outputting a photoacoustic signal from said particular particulate substance.

58. An apparatus according to claim 57, wherein said particulate substance is an immunoreaction product between an antigen and an antibody or between the antigen and a material support the antibody thereon.

59. An apparatus according to claim 58, wherein the ray of light to be radiated to said particulate substance is a ray of continuous light within a wavelength range capable of embracing the particle size distribution of said particulate substance.

60. An apparatus according to claim 58, wherein said support material for said antibody is a material having a small light absorption coefficient for the wavelength of the ray of light to be radiated.

61. An apparatus according to claim 57, wherein said particulate substance is an immunoreaction product between an antibody and an antigen or between the antibody and a material support the antigen thereon.

62. An apparatus according to claim 61, wherein the ray of light to be radiated to said particulate substance is a ray of continuous light within a wavelength range capable of embracing the particle size distribution of said particulate substance.

63. An apparatus according to claim 61, wherein said support material for said antibody is a material having a small light absorption coefficient for the wavelength of the ray of light to be radiated.

64. An apparatus according to claim 57, wherein the ray of light to be radiated to said particulate substance is a ray of continuous light within a wavelength range capable of embracing the particle size distribution of said particulate substance.

* * * * *